(12) United States Patent
Doerr et al.

(10) Patent No.: US 8,676,327 B2
(45) Date of Patent: Mar. 18, 2014

(54) NEUROSTIMULATOR

(75) Inventors: Thomas Doerr, Berlin (DE); Ingo Weiss, Berlin (DE); Andreas Neumann, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 1312 days.

(21) Appl. No.: 12/402,821

(22) Filed: Mar. 12, 2009

(65) Prior Publication Data
US 2009/0264953 A1   Oct. 22, 2009

(30) Foreign Application Priority Data

Apr. 22, 2008   (DE) .......................... 10 2008 020 070

(51) Int. Cl.
*A61N 1/00*   (2006.01)
(52) U.S. Cl.
USPC .......................................................... 607/45
(58) Field of Classification Search
USPC .......................................................... 607/45
See application file for complete search history.

(56) References Cited

U.S. PATENT DOCUMENTS

| 5,928,272 | A | 7/1999 | Adkins et al. | |
|---|---|---|---|---|
| 6,128,537 | A | 10/2000 | Rise | |
| 6,473,644 | B1 * | 10/2002 | Terry et al. | 607/2 |
| 2004/0133248 | A1 * | 7/2004 | Frei et al. | 607/45 |
| 2005/0021104 | A1 * | 1/2005 | DiLorenzo | 607/45 |
| 2005/0154424 | A1 | 7/2005 | Tass | |
| 2007/0148273 | A1 | 6/2007 | Reeve | |
| 2007/0173901 | A1 | 7/2007 | Reeve | |
| 2007/0260289 | A1 * | 11/2007 | Giftakis et al. | 607/45 |
| 2008/0033490 | A1 | 2/2008 | Giftakis et al. | |
| 2008/0071327 | A1 * | 3/2008 | Miesel et al. | 607/59 |

FOREIGN PATENT DOCUMENTS

DE   102 11 765   10/2003

OTHER PUBLICATIONS

German Search Report, dated Jan. 27, 2009.
European Search Report, dated Jul. 27, 2009.

* cited by examiner

*Primary Examiner* — Christopher D Koharski
*Assistant Examiner* — Roland Dinga
(74) *Attorney, Agent, or Firm* — ARC IP Law, PC; Joseph J. Mayo

(57) ABSTRACT

Neurostimulator (20) comprising a signal generator (40) for generating stimulation pulses, connected or connectable to at least one electrode (10) implantable in the brain of a patient, comprising a signal generator control unit (36) connected to the signal generator (40) and designed to control the delivery of stimulation pulses and to make adjustments in signal generator settings as needed, comprising a device connected to the signal generator control unit (36) for determination and analysis of the heart rate of a patient (30, 32, 34), characterized in that the signal generator control unit (36) is designed to check on the health status of a patient and/or the success of a treatment using at least one heart-rate-dependent characteristic quantity determined by the device for determination and analysis of the heart rate (30, 32, 34) and to make an adjustment in the signal generator settings if necessary.

17 Claims, 3 Drawing Sheets

NEUROSTIMULATOR

This application takes priority from German Patent Application DE 10 2008 020 070.0, filed 22 Apr. 2008, the specification of which is hereby incorporated herein by reference.

BACKGROUND OF THE INVENTION

1. Field of the Invention

The invention relates to an implantable neurostimulator for temporary stimulation of body tissue, in particular for brain stimulation (deep brain stimulation, DBS).

2. Description of the Related Art

The area of use of such instruments has been neurological diseases in particular, such as Parkinson's disease or depression.

In principle, neurostimulators for such fields of application are known from the state of the art, but they have a number of disadvantages. One of these disadvantages is that known neurostimulators for such indications perform treatment regardless of the patient's current health condition.

BRIEF SUMMARY OF THE INVENTION

The present invention is based on the object of preferably eliminating at least some of the disadvantages that arise as a result of the state of the art.

This object is achieved by the invention through an implantable neurostimulator comprising the following components:
- a signal generator for generating stimulation pulses, connectable or connected to at least one electrode implantable in a patient's brain,
- a signal generator control unit that is connected to the signal generator and is designed to control the delivery of stimulation pulses and to make adjustments in signal generator settings as needed, and
- a device connected to the signal generator control unit, for determination and analysis of a patient's heart rate.

According to the invention, the signal generator control unit is designed to check on a patient's health status and/or the success of a treatment by using at least one heart-rate-dependent characteristic quantity determined by the device for determination and analysis of the heart rate and, if necessary, to make an adjustment in the signal generator settings.

One advantage of the inventive neurostimulator is that the acute health status of a patient has an effect on the signal generator settings and therefore on the treatment. For example, if the patient requires a lower stimulation amplitude based on his acute health status, the power output by the neurostimulator can be reduced by adjusting the signal generator settings, and thereby prolonging the lifetime of the battery of the neurostimulator.

The signal generator, the signal generator control unit and the device for determination and analysis of the heart rate are preferably accommodated together with a battery in an implantable liquid-tight housing.

According to the invention, the neurostimulator has at least one terminal for connection of an implantable electrode or is fixedly connected to the neurostimulator via an electric line.

According to an especially preferred embodiment variant, the neurostimulator is designed to detect a patient's heart rate via the lead of an electrocardiogram (ECG). The electrocardiogram has proven to be an especially simple and reliable method for determining a patient's heart rate.

According to an alternative embodiment, the neurostimulator is designed to determine a patient's heart rate by analyzing the pulse.

If the heart rate is determined via the lead of an ECG, then the neurostimulator is preferably designed to calculate the heart rate based on the time intervals of the R waves.

The heart rate is understood to refer to the period between two heart beats, i.e., the so-called "beat-to-beat" rate.

According to an especially preferred embodiment of the invention, the neurostimulator is designed to derive an ECG between the housing of the neurostimulator and the electrode that is connected and/or connectable to the stimulator.

For this purpose, at least a portion of the surface of the housing is designed as a sensing electrode.

To derive the heart rate from the ECG, the neurostimulator is preferably designed to sample and digitize the ECG at a frequency of $\geq 500$ Hz in the first step. The neurostimulator is preferably designed to calculate the heart rate from the digitized ECG over the intervals of time of the R waves.

The neurostimulator is preferably designed to further process the heart rates calculated during a predefined period (hereinafter also referred to as the analysis period) to yield a heart-rate-dependent characteristic quantity. With the help of such a characteristic quantity, the patient's current health status is ascertained according to the invention and/or the success of a treatment is checked.

The neurostimulator or, more specifically, the device for determination and analysis of the heart rate, is especially preferably designed to calculate a characteristic quantity of the heart rate variability (HRV) derived from the frequency range.

According to an alternative embodiment variant, the neurostimulator and/or the device for determination and analysis of the heart rate is/are designed to calculate a characteristic quantity of the heart rate variability derived from the time range.

A number of variables derived from the time range as well as variables derived from the frequency range are already known from the state of the art, and it should be pointed out here that each of these characteristic quantities or each combination of such characteristic quantities may essentially be used to ascertain a patient's current health status or to check on the success of a treatment, thereby yielding additional advantageous embodiments of the invention that are not mentioned here explicitly.

For treatment of patients with severe depression, however, it has been found that a neurostimulator designed to calculate the current health status with the help of the HRV characteristic quantity RMSSD (root mean square successive differences between neighboring NN intervals; higher values indicate increased parasympathetic activity) is especially effective.

To also be able to perform a classification of a health status with a characteristic quantity and/or to be able to perform a required adjustment in the signal generator settings, the neurostimulator preferably has a memory unit in which reference values are saved (e.g., in a list).

With the help of such reference values, a certain health status may be determined for each characteristic quantity and/or the required adjustments in the signal generator settings may be performed.

In order not to have to perform a classification of the health status with the help of the reference values for each characteristic quantity calculated, another embodiment variant is designed to also save the characteristic quantities of a preceding analytical period in addition to the reference values. Before performing a classification of a health status on the basis of the characteristic quantity thereby ascertained, this embodiment variant is designed to first perform a comparison of the characteristic quantities actually determined with the characteristic quantity of the preceding analytical period. If the difference between these characteristic quantities exceeds a threshold value, then the neurostimulator is designed so that it will not perform a subsequent classification of a health status and/or adaptation of the signal generator settings.

According to a special embodiment variant, the inventive neurostimulator is designed not to compare the current characteristic quantity with the characteristic quantity of a preceding analytical period but instead to compare it with a characteristic quantity which is determined at a specific time of day or night and has been saved. However, a comparison of a characteristic quantity that has just been calculated with the characteristic quantity of an earlier analytical period may always serve only for a relative assessment of the health status and cannot provide any qualitative information about the health status. For a qualitative assessment of a patient's health status, a classification with the above-mentioned reference values is always necessary.

According to a preferred embodiment variant, the reference values are not immutable, but instead the neurostimulator is designed to update the reference values, e.g., at regular intervals or by request, according to another embodiment variant.

To this end, according to another embodiment variant, a telemetry device is also provided for the neurostimulator to allow changes and/or more extensive analyses via an external device.

According to another embodiment variant, the neurostimulator additionally has an accelerometer designed to determine a patient's physical activity in the form of a characteristic quantity and to use this value to determine the patient's current status in addition to using the characteristic quantity for the heart rate variability HRV.

For example, the HRV of a patient at rest is different from the HRV of a patient performing athletics, even assuming the same health status, so determination of the current health status using a characteristic quantity for the patient's physical activity can provide a more accurate result.

In this context, the control unit is designed to adapt either the algorithm for calculating the heart-rate-dependent characteristic quantity or to adapt the reference value for determination of the acute health status according to the characteristic quantity determined for the patient's activity.

According to the embodiment variant described previously, the neurostimulator is always designed to perform the required adjustments in the signal generator settings after an analysis of heart-rate-dependent characteristic quantities.

However, according to another embodiment variant, the neurostimulator is also designed to first perform a predefined stimulation therapy and then to check its results in a second step.

According to a special embodiment, a neurostimulator provided for the depression therapy already described above is designed to perform the following work steps in succession:

First, the characteristic quantity RMSSD is determined and saved in a predetermined time window on each of five days of the week with the starting amplitude just set. On the sixth day of the week, an RMSSD calculation is performed while the neurostimulator is performing its stimulation with an increased amplitude. If the SDANN value calculated during this measurement is significantly greater than the mean value of the RMSSD values determined previously, then the preset stimulation amplitude is considered to be too low and therefore the elevated stimulation amplitude from the test on day 6 is set permanently; otherwise the old setting is retained. Next on the seventh day of the week, an RMSSD calculation is performed while the neurostimulator is performing its stimulation with a reduced amplitude. If the RMSSD value plus a defined tolerance is within the range of the reference values on days 1-5, then the reduced stimulation amplitude is considered to be effective and the permanent stimulation amplitude is reduced accordingly. If the RMSSD value calculated during this measurement is significantly smaller than the mean value of the RMSSD values determined previously, then the tested stimulation amplitude is considered to be too low and therefore the active value for the stimulation amplitude before this test is set again.

BRIEF DESCRIPTION OF THE DRAWINGS

Other aspects of the inventive implant and various embodiment variants are explained in greater detail on the basis of the drawings, in which.

DETAILED DESCRIPTION OF THE INVENTION

Figure 1:
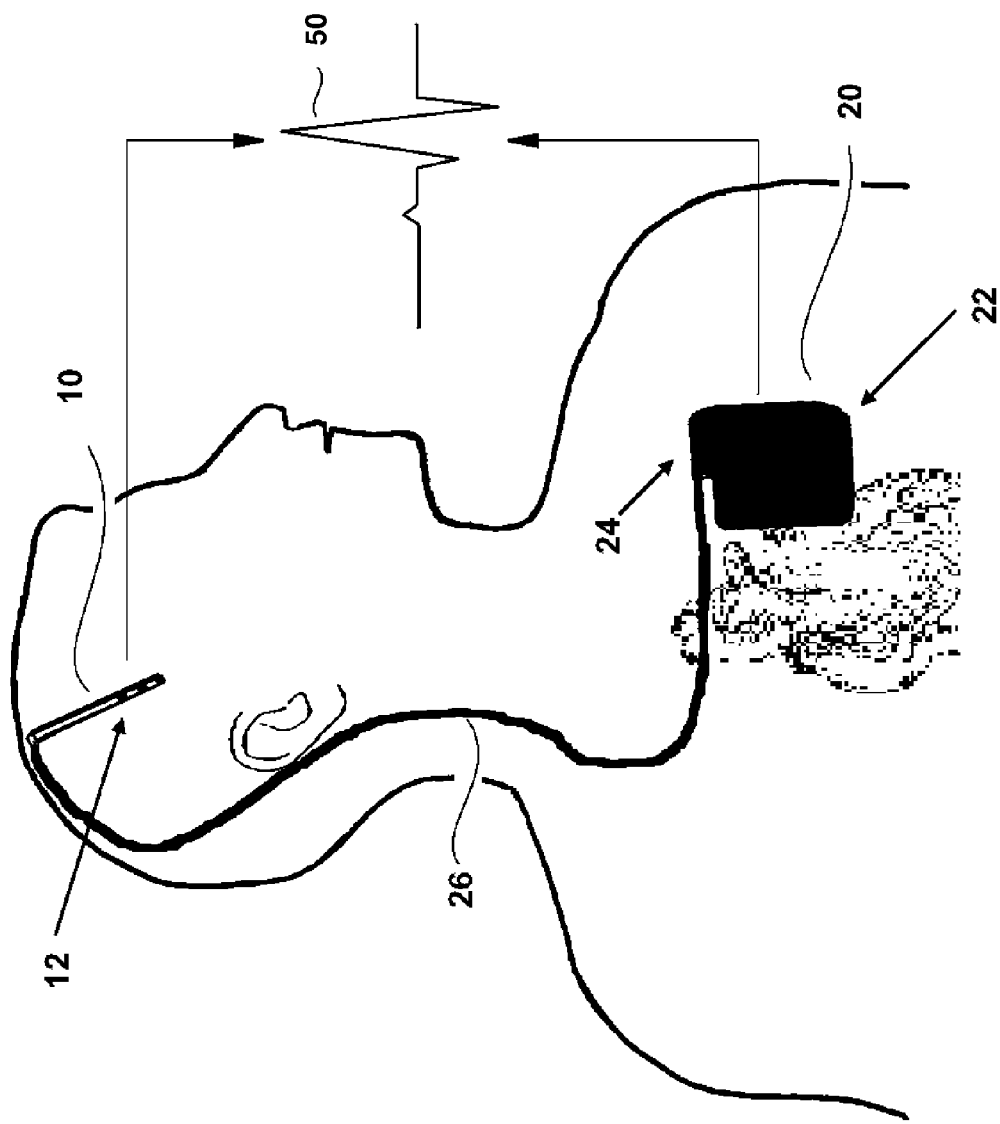
FIG. 1 shows a basic diagram of implantation of the inventive neurostimulator in a patient's body.

FIG. 1 shows an implantable neurostimulator 20 with a housing 22 and a header 24. The housing 22 is hollow and has a surface that is at least partially electrically conductive. The housing 22 is typically made of a biocompatible metal such as titanium. The housing 22 contains a battery and electronic components of the neurostimulator 20. The header 24 contains connecting bushings, e.g., for a feeder line 26.

An electrode 10 for deep brain stimulation (DBS) is electrically connected to at least one terminal bushing in the header 24 via a feeder line 26. The electrode 10 here has multiple electrode poles by which stimulating pulses 50 can be delivered in the event of treatment.

At least one of the electrode poles 12 together with the electrically conductive section of the housing forms an electrode pair for deriving an electrocardiogram (ECG). At least one of the electrode poles 12 and the conductive surface of the housing 22 are connected to an ECG signal processing unit 30 (not visible here) in the interior of the housing 22 of the neurostimulator 20 (details described with respect to FIG. 2).

During use, the electrode 10 to be connected to the neurostimulator 20 for deep brain stimulation is positioned in the patient's brain in such a way that the target region of stimulation for treatment of Parkinson's disease is the subthalamic nucleus or for essential tremor is the ventral thalamus and/or for dystonia is the globus pallidus. The nucleus accumbens is the target region for stimulation for treatment of depression.

If the neurostimulator 20 and the electrode 10 connected to it are implanted in a patient, an ECG is derived either continuously or temporarily between the corresponding site of treatment in the patient's brain and the site where the housing 22 is positioned (e.g., beneath the pectoral muscles) and is analyzed in a heart-rate analyzer unit (not shown here) inside the housing 22.

Figure 2:
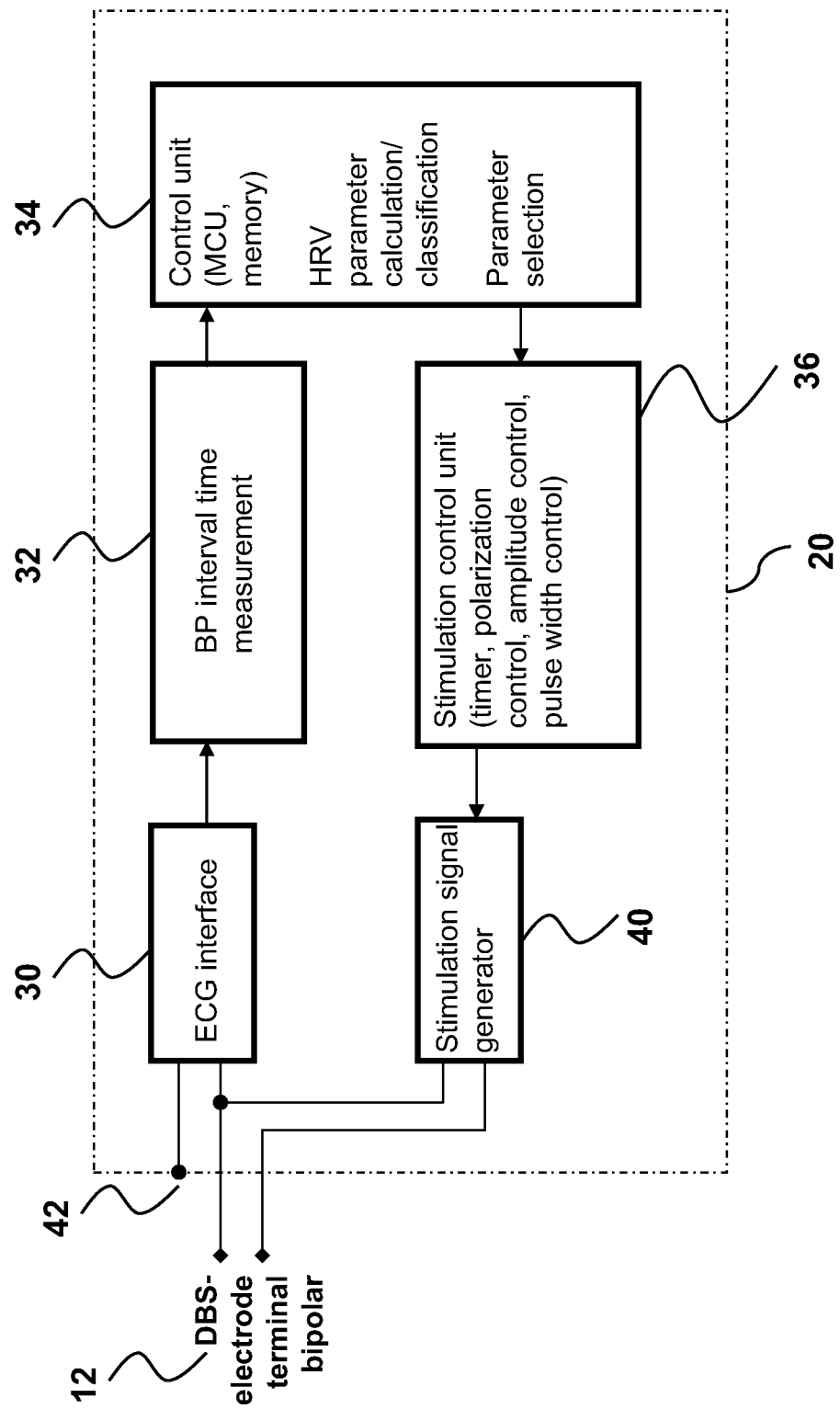
FIG. 2 shows a block diagram of an embodiment variant of the inventive neurostimulator with ECG control.

As already explained in detail with regard to FIG. 2, the corresponding target regions in a patient's brain are stimulated either when this is an acute necessity because of a patient's health status or continuously according to predefined signal generator settings.

FIG. 2 shows a schematic block diagram of the electronic components of the neurostimulator 20 arranged inside the housing 22.

In the embodiment variant shown here, the neurostimulator 20 comprises an ECG signal processing unit 30, a heart-rate measuring unit 32 and a heart-rate analyzer unit 34, which together constitute the inventive device for determination and analysis of the heart rate. In addition, the neurostimulator 20 comprises a signal generator control unit 36 and a signal generator 40 and is connected to two stimulation electrode poles 12 and a sensing electrode 42.

For therapy control and/or for adjustment of the settings of the signal generator 40, the patient's ECG is first derived between a pole 12 of the brain electrode 10 and the sensing electrode 42 of the neurostimulator by means of the ECG signal processing unit 30.

The ECG signal processing unit 30 makes available a signal representing one heartbeat (R wave) to the heart-rate measuring unit 32.

The heart-rate measuring unit 32 determines the interval of time between the R waves and makes this information—namely the heart rate—available to the heart-rate analyzer unit 34.

During a fixed analytical period, the heart-rate analyzer unit 34 in this way receives a plurality of successive heart rates from which it calculates one or more characteristic quantities of heart rate variability. Since the heart-rate analyzer unit 34, which is designed as a microprocessor-controlled module, has calculated one or more characteristic quantities of heart-rate variability such as SDANN (standard deviation of the average of the NN intervals in all five minutes of the total recording), it makes them available to the signal generator control unit 36.

The signal generator control unit comprises a short-term memory unit (not visible here) and a long-term memory unit (also not visible here).

In the long-term memory unit, a classification table is stored, so that a health status and/or certain generator settings are assigned to each characteristic quantity therein.

In the short-term memory unit, each characteristic quantity received from the heart-rate analyzer unit 34 is saved for the duration of at least one analytical period, to be retrievable on receipt of the next characteristic quantity.

To decide whether the settings of the signal generator 40 must be adjusted, a characteristic quantity that has just been determined is compared in a first step with the stored characteristic quantity of the preceding analytical period and a difference is formed.

If this difference is greater than or less than a fixed limit value for two successive analytical periods, then it is known whether an adjustment of the signal generator settings must be performed.

The adjustment of the signal generator settings is performed in a second step in which the characteristic quantity just determined is assigned to a certain health status and/or to certain signal generator settings with the help of the classification table saved in the long-term memory.

Figure 3:
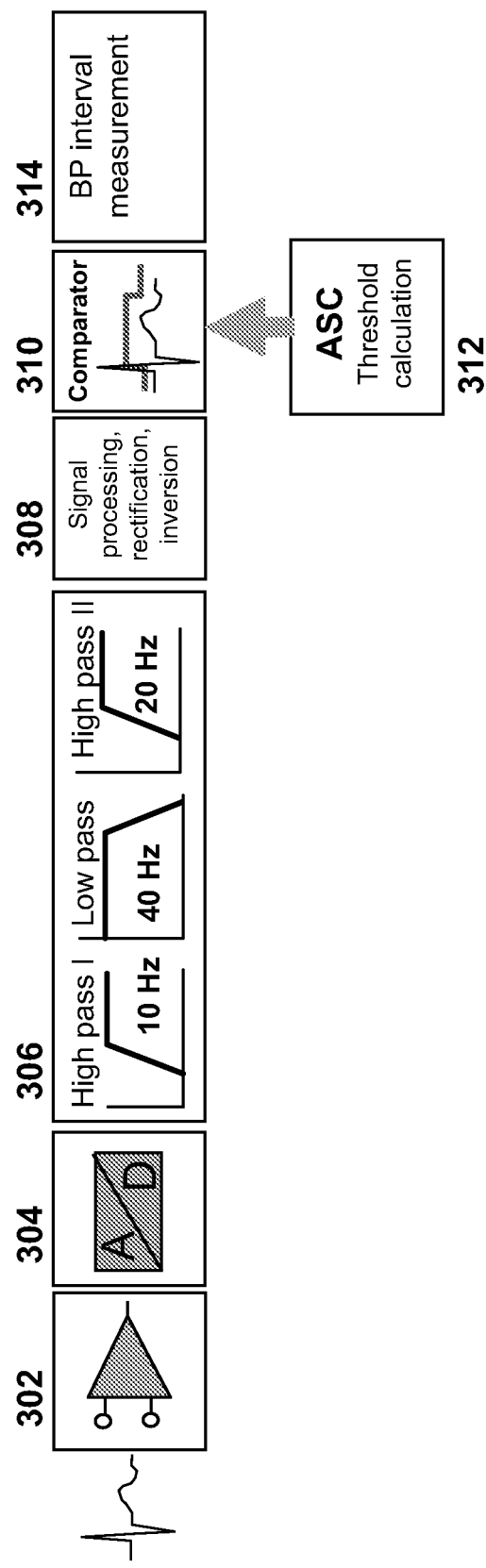
FIG. 3 shows a block diagram illustrating an ECG signal processing unit and a heart-rate measurement unit.

FIG. 3 shows a detailed block diagram of the individual components of the ECG signal processing unit 30 and the heart-rate measuring unit 32.

After ECG signal amplification (302), digitization (304) of the input signal is performed at a sampling rate of at least 500 Hz but preferably more than 1 kHz. Then digital signal filtering is performed using a programmable 3-stage digital filter (306), wherein a filter cascade comprising a first high-pass filter, a low-pass filter and a second high-pass filter of the first order is provided in the exemplary embodiment, thereby filtering out the R wave as the useful signal.

In a subsequent signal conditioning step (308) half-wave rectification of the filtered signal is performed, optionally activating an automatic switch to the half-wave having the greatest amplitude of the useful signal. In the downstream comparator (310), R waves are recognized by threshold value comparison.

The comparative thresholds are dynamically adapted to the useful signal amplitude. This adaptation is performed by a programmable control unit (312) for threshold determination. In the downstream time measuring unit (314), the interval of the R waves thus determined by the comparator (310) is measured with a time base of equal to or less than 10 ms.

What is claimed is:

1. An implantable neurostimulator (20) for treatment of patients, in particular those having Parkinson's disease or depression, comprising:
   a signal generator (40) configured to generate stimulation pulses, connected or connectable to at least one electrode (10) implantable in a brain of a patient;
   a signal generator control unit (36) connected to the signal generator (40) and designed to control a delivery of stimulation pulses and to make adjustments in signal generator settings as needed;
   a device configured to determine and analyze a heart rate (30, 32, 34) of the patient, wherein said device is connected to the signal generator control unit (36);
   wherein the signal generator control unit (36) is configured to check on
      a health status of the patient or a success of a treatment or
      a health status of the patient and a success of a treatment based on
      at least one heart-rate-dependent characteristic quantity determined at a specific time of day or night by the device configured to determine and analyze the heart rate (30, 32, 34) and,
   compare said at least one heart-rate-dependent characteristic quantity determined at said specific time of day or night with a previously saved at least one heart-rate-dependent characteristic quantity from a corresponding said specific time of day or night, to make an adjustment of the signal generator settings; and,
   wherein said at least one heart-rate-dependent characteristic quantity comprises a root mean ware successive differences or RMSSD between neighboring NN intervals.

2. The neurostimulator (20) according to claim 1, wherein the signal generator (40), the signal generator control unit (36) and the device for determination and analysis of the heart rate (30, 32, 34) are accommodated together with a battery in an implantable fluid-tight housing (22).

3. The neurostimulator (20) according to claim 1, wherein the neurostimulator (20) is configured to determine the heart rate and derive an electrocardiogram.

4. The neurostimulator (20) according to claim 3 comprising an at least partially electrically conductive housing, which is configured to derive the electrocardiogram between a brain electrode and a housing (22).

5. The neurostimulator (20) according to claim 3, wherein the neurostimulator (20) is configured to sample and to digitize a derived electrocardiogram at a frequency of $\geq$500 Hz.

6. The neurostimulator (20) according to claim 1, wherein the at least one heart-rate-dependent characteristic quantity is a frequency-range-derived variable of a heart rate variability.

7. The neurostimulator (20) according to claim 1, wherein the at least one heart-rate-dependent characteristic quantity is a time-range-derived variable of a heart rate variability.

8. The neurostimulator (20) according to claim 1, comprising a memory unit that is connected to the signal generator control unit (36) and is configured to store the at least one heart-rate-dependent characteristic quantity.

9. The neurostimulator (20) according to claim 1, comprising a memory unit that is connected to the signal generator control unit (36), such that the signal generator control unit (36) is configured to assign the health status and/or certain signal generator settings to each characteristic quantity with help of a classification table stored in the memory unit, in which certain health statuses and/or the certain signal generator settings are assigned to a number of reference values.

10. The neurostimulator (20) according to claim 1, wherein the neurostimulator (20) is configured to assign the health status and/or certain signal generator settings to a characteristic quantity only when a difference between
    a characteristic quantity that has just been calculated and
    a characteristic quantity calculated and stored at an earlier point in time exceeds or falls below a certain limit value.

11. The neurostimulator (20) according to claim 1, wherein the neurostimulator (20) is configured to check on the success of the treatment with a new signal generator setting wherein the neurostimulator (20) is further configured to
    first form a difference between a characteristic quantity that has been calculated and an average value of several characteristic quantities calculated and stored at a previous point in time; and,
    then compare the difference with a limit value.

12. The neurostimulator (20) according to claim 1, comprising an accelerometer designed to determine an activity of the patient in a form of a characteristic quantity.

13. The neurostimulator (20) according to claim 12, wherein the characteristic quantity based on the activity of the patient is used to determine the health status and/or to adjust the signal generator settings.

14. An implantable neurostimulator (20) for treatment of patients, in particular those having Parkinson's disease or depression, comprising:
    a signal generator (40) configured to generate stimulation pulses, connected or connectable to at least one electrode (10) implantable in a brain of a patient;
    a signal generator control unit (36) connected to the signal generator (40) and designed to control a delivery of stimulation pulses and to make adjustments in signal generator settings as needed;
    a device configured to determine and analyze a heart rate (30, 32, 34) of the patient, wherein said device is connected to the signal generator control unit (36);
    an accelerometer configured to determine an activity of the patient in a form of a characteristic quantity;
    wherein the signal generator control unit (36) is configured to check on
        a health status of the patient or a success of a treatment or
        a health status of the patient and a success of a treatment based on
        said characteristic quantity derived from said accelerometer and
        at least one heart-rate-dependent characteristic quantity determined at a specific time of day or night by the device configured to determine and analyze the heart rate (30, 32, 34); and,
    compare said at least one heart-rate-dependent characteristic quantity determined at said specific time of day or night with a previously saved at least one heart-rate-dependent characteristic quantity from a corresponding said specific time of day or night, to make an adjustment of the signal generator settings;
    wherein said at least one heart-rate-dependent characteristic quantity comprises a root mean square successive differences or RMSSD between neighboring NN intervals; and,
    wherein said signal generator control unit (36) is configured to save said RMSSD for each of five days of a week and on a sixth day of said week, calculate a current RMSSD while said neurostimulator performs a stimulation at an increased amplitude that is higher than an original amplitude, wherein if a standard deviation of the average of the NN intervals or SDANN is significantly greater than a mean value of RMSSD for said five days of said week, then a preset stimulation amplitude is determined to be too low and said increased amplitude is set for subsequent use, otherwise said original amplitude is set for said subsequent use.

15. The neurostimulator (20) according to claim 14, wherein said signal generator control unit (36) is configured to calculate a current RMSSD while said neurostimulator performs a stimulation at a decreased amplitude, wherein if said RMSSD plus a defined tolerance is within a range of said RMSSD for each of said five days of said week, then said preset stimulation amplitude is determined to be too high and said decreased amplitude is set for subsequent use, otherwise if said current RMSSD is significantly smaller than said mean value of said RMSSD for said five days of said week, then said preset stimulation amplitude is set for subsequent use.

16. The neurostimulator (20) according to claim 14, wherein the characteristic quantity based on the activity of the patient is used to determine the health status and/or to adjust the signal generator settings.

17. An implantable neurostimulator (20) for treatment of patients, in particular those having Parkinson's disease or depression, comprising:
    a signal generator (40) configured to generate stimulation pulses, connected or connectable to at least one electrode (10) implantable in a brain of a patient;
    a signal generator control unit (36) connected to the signal generator (40) and designed to control a delivery of stimulation pulses and to make adjustments in signal generator settings as needed;
    a device configured to determine and analyze a heart rate (30, 32, 34) of the patient, wherein said device is connected to the signal generator control unit (36);
    an accelerometer configured to determine an activity of the patient in a form of a characteristic quantity;
    wherein the characteristic quantity based on the activity of the patient is used to determine the health status and/or to adjust the signal generator settings; and,
    wherein the signal generator control unit (36) is configured to check on
        a health status of the patient or a success of a treatment or
        a health status of the patient and a success of a treatment based on
        said characteristic quantity derived from said accelerometer and
        at least one heart-rate-dependent characteristic quantity determined at a specific time of day or night by the device configured to determine and analyze the heart rate (30, 32, 34);
    compare said at least one heart-rate-dependent characteristic quantity determined at said specific time of day or night with a previously saved at least one heart-rate-dependent characteristic quantity from a corresponding said specific time of day or night, to make an adjustment of the signal generator settings;

wherein said at least one heart-rate-dependent characteristic quantity comprises a root mean square successive differences or RMSSD between neighboring NN intervals;

wherein said signal generator control unit (36) is configured to save said RMSSD for each of five days of a week and on a sixth day of said week, calculate a current RMSSD while said neurostimulator performs a stimulation at an increased amplitude that is higher than an original amplitude, wherein if a standard deviation of the average of the NN intervals or SDANN is significantly greater than a mean value of RMSSD for said five days of said week, then a preset stimulation amplitude is determined to be too low and said increased amplitude is set for subsequent use, otherwise said original amplitude is set for said subsequent use; and, wherein said signal generator control unit (36) is configured to calculate a current RMSSD while said neurostimulator performs a stimulation at a decreased amplitude, wherein if said RMSSD plus a defined tolerance is within a range of said RMSSD for each of said five days of said week, then said preset stimulation amplitude is determined to be too high and said decreased amplitude is set for subsequent use, otherwise if said current RMSSD is significantly smaller than said mean value of said RMSSD for said five days of said week, then said preset stimulation amplitude is set for subsequent use.

* * * * *